US011086297B2

United States Patent
Bertaux Hegemann (10) Patent No.: US 11,086,297 B2
(45) Date of Patent: Aug. 10, 2021

(54) METHODS AND SYSTEMS FOR FABRICATING, EVALUATING AND IMPROVING THERAPEUTIC COMPRESSION GARMENTS

(71) Applicant: SIGVARIS AG, St. Gallen (CH)

(72) Inventor: Emilie Bertaux Hegemann, St. Gallen (CH)

(73) Assignee: SIGVARIS AG, St. Gallen (CH)

(*) Notice: Subject to any disclaimer, the term of this patent is extended or adjusted under 35 U.S.C. 154(b) by 142 days.

(21) Appl. No.: 16/208,675

(22) Filed: Dec. 4, 2018

(65) Prior Publication Data

US 2020/0174453 A1 Jun. 4, 2020

(51) Int. Cl.
G06K 9/00 (2006.01)
G05B 19/4155 (2006.01)
A61B 5/107 (2006.01)
A61B 5/00 (2006.01)
A61F 13/08 (2006.01)

(52) U.S. Cl.
CPC ........ *G05B 19/4155* (2013.01); *A61B 5/1077* (2013.01); *A61B 5/1079* (2013.01); *A61B 5/4878* (2013.01); *A61F 13/08* (2013.01); G05B 2219/45196 (2013.01)

(58) Field of Classification Search
CPC ... A61B 5/1079; A61B 5/4878; A61B 5/1077; G05B 19/4155; G05B 2219/45196; A61F 13/08
USPC .......................................................... 382/111
See application file for complete search history.

(56) References Cited

U.S. PATENT DOCUMENTS

| | | |
|---|---|---|
| 2,687,723 A | 8/1954 | Stern |
| 3,613,679 A | 10/1971 | Bijou |
| 3,856,008 A | 12/1974 | Fowler et al. |
| D234,271 S | 2/1975 | Moore |
| 4,215,687 A | 8/1980 | Shaw |
| 4,367,733 A | 1/1983 | Stromgren |
| D269,816 S | 7/1983 | Meier et al. |
| 4,476,857 A | 10/1984 | Levine |
| 5,108,455 A | 4/1992 | Telikicherla |
| 5,254,122 A | 10/1993 | Shaw |
| D353,005 S | 11/1994 | Glidden |
| D382,344 S | 8/1997 | Swedberg et al. |
| 5,904,145 A | 5/1999 | Reid |
| 5,906,206 A | 5/1999 | Shaw et al. |
| 6,152,893 A | 11/2000 | Pigg et al. |
| 6,196,231 B1 | 3/2001 | Reid |

(Continued)

FOREIGN PATENT DOCUMENTS

| | | |
|---|---|---|
| AU | 6414174 A | 7/1975 |
| AU | 2017329457 A1 | 2/2019 |

(Continued)

OTHER PUBLICATIONS

European Search Report issued in corresponding EP Application No. 19210930.4 dated Feb. 28, 2020.

(Continued)

*Primary Examiner* — Huy C Ho (74) *Attorney, Agent, or Firm* — FisherBroyles LLP; Anthony J. DoVale; John Boyd (57) ABSTRACT

Systems and methods for designing, fabricating, selecting, evaluating and/or improving therapeutic compression garments for patients or individuals using compression garments.

19 Claims, 2 Drawing Sheets

(56) References Cited

U.S. PATENT DOCUMENTS

| | | |
|---|---|---|
| 6,254,554 B1 | 7/2001 | Turtzo |
| 6,338,723 B1 | 1/2002 | Carpenter et al. |
| 6,516,804 B1 | 2/2003 | Hoffman |
| 7,329,232 B2 | 2/2008 | Lipshaw et al. |
| 8,801,645 B2 | 8/2014 | Lipshaw et al. |
| D717,453 S | 11/2014 | Mahtani |
| D728,804 S | 5/2015 | Hansen |
| 9,364,701 B2 | 6/2016 | Bartsch |
| 9,642,559 B2 | 5/2017 | Falconio-West et al. |
| 9,642,766 B2 | 5/2017 | Lipshaw et al. |
| D800,325 S | 10/2017 | Cox |
| 10,045,581 B2 | 8/2018 | Weiler et al. |
| 10,076,462 B2 | 9/2018 | Johnson et al. |
| D848,625 S | 5/2019 | Chase et al. |
| D850,632 S | 6/2019 | Chiang et al. |
| D872,286 S | 1/2020 | Hoffman et al. |
| 2002/0062096 A1 | 5/2002 | Bennett |
| 2005/0113729 A1 | 5/2005 | Scott et al. |
| 2005/0148917 A1 | 7/2005 | Nathanson |
| 2005/0192524 A1 | 9/2005 | Lipshaw et al. |
| 2006/0201032 A1 | 9/2006 | Ramsey |
| 2007/0179421 A1 | 8/2007 | Farrow |
| 2010/0269240 A1 | 10/2010 | Weir et al. |
| 2010/0312160 A1 | 12/2010 | Creighton et al. |
| 2011/0125183 A1 | 5/2011 | Lipshaw et al. |
| 2011/0185508 A1 | 8/2011 | Hsu et al. |
| 2011/0257575 A1 | 10/2011 | Farrow et al. |
| 2012/0179084 A1 | 7/2012 | Lipshaw et al. |
| 2012/0277073 A1 | 11/2012 | Bartsch |
| 2013/0283500 A1 | 10/2013 | Lipshaw et al. |
| 2013/0319128 A1 | 12/2013 | Richardson et al. |
| 2015/0025424 A1 | 1/2015 | Richardson et al. |
| 2016/0000612 A1 | 1/2016 | Cox |
| 2016/0030251 A1 | 2/2016 | Schuren et al. |
| 2016/0030267 A1 | 2/2016 | Lipshaw et al. |
| 2016/0100988 A1 | 4/2016 | Vee et al. |
| 2016/0166458 A9 | 6/2016 | Lipshaw et al. |
| 2016/0220200 A1* | 8/2016 | Sandholm ............ A61B 5/7246 |
| 2016/0235354 A1 | 8/2016 | Weiler et al. |
| 2017/0258672 A1 | 9/2017 | Wennen et al. |
| 2018/0042322 A1* | 2/2018 | Weiler .................. G16H 50/20 |
| 2018/0168261 A1 | 6/2018 | Weiler et al. |
| 2018/0243143 A1 | 8/2018 | Karadsheh |
| 2018/0344532 A1 | 12/2018 | Karadsheh et al. |
| 2019/0133229 A1 | 5/2019 | Hoffman et al. |
| 2019/0209387 A1 | 7/2019 | Ganzoni |
| 2019/0216653 A1 | 7/2019 | Ganzoni |

FOREIGN PATENT DOCUMENTS

| | | |
|---|---|---|
| AU | 2017329458 A1 | 2/2019 |
| AU | 2018223706 A1 | 8/2019 |
| BR | 112019002388 A2 | 6/2019 |
| BR | 112019002399 A2 | 6/2019 |
| CA | 2 722 146 A1 | 10/2009 |
| CA | 3 037 413 A1 | 3/2018 |
| CA | 3 037 417 A1 | 3/2018 |
| CA | 3 054 339 A1 | 8/2018 |
| CH | 712 938 A1 | 3/2018 |
| CH | 712 939 A1 | 3/2018 |
| EP | 1 052 319 A1 | 11/2000 |
| EP | 1731096 A1 | 12/2006 |
| EP | 1 959 880 A1 | 8/2008 |
| EP | 3 512 478 A1 | 7/2019 |
| EP | 3 512 479 A1 | 7/2019 |
| EP | 3 565 515 A1 | 11/2019 |
| FR | 2 961 389 A1 | 12/2011 |
| MX | 2019001588 A | 9/2019 |
| MX | 2019001642 A | 9/2019 |
| MX | 2019009113 A | 9/2019 |
| WO | 99/30607 A2 | 6/1999 |
| WO | 00/15139 A2 | 3/2000 |
| WO | 01/89410 A2 | 11/2001 |
| WO | 2003040449 A1 | 5/2003 |
| WO | 2005/052235 A1 | 6/2005 |
| WO | 2005106087 A1 | 11/2005 |
| WO | 95/16416 A1 | 8/2008 |
| WO | 2013/085445 A1 | 6/2013 |
| WO | 2013/138394 A1 | 9/2013 |
| WO | 2014/116497 A1 | 7/2014 |
| WO | 2014/160572 A1 | 10/2014 |
| WO | 2015/188158 A2 | 12/2015 |
| WO | 2016/048827 A1 | 3/2016 |
| WO | 2016/105213 A1 | 6/2016 |
| WO | 2018/054681 A1 | 3/2018 |
| WO | 2018/054682 A1 | 3/2018 |
| WO | 2018/153611 A1 | 8/2018 |
| WO | 2019/091811 A1 | 5/2019 |

OTHER PUBLICATIONS

CircAid JuxtaFit Essentials arm sleeve by Medi; http://mediusa.com/portfolio-item/juxtafit-essentials-upper-extremity/; Mar. 29, 2015.

CircAid Arm Reduction Kit by Medi; http://mediusa.com/portfolio-item/circaid-reduction-kit/; May 20, 2016.

Solaris ReadyWrap arm sleeve by Lohmann & Rauscher; http://www.lymphedemaproducts.com/products/readywrap-arm.html; May 4, 2017.

Solaris TributeWrap Wrist to Axilla; https://www.lohmann-rauscher.com/us-en/products/solaris-collection-by-lr/tributewrap/; date unknown, at least prior to applicant's filing date of Feb. 1, 2018.

FarrowWrap Lite OTS Armpiece by Jobst; http://www.jobst-usa.com/product/jobst-farrow-ots-armsleeve/; Jul. 14, 2017.

FarrowWrap Lite Trim-To-Fit Armpiece by Jobst; http://www.jobst-usa.com/product/jobst-farrowwrap-lite-armpiece/; Jul. 14, 2017.

FarrowWrap Classic Custom Armpiece by Jobst; http://www.jobst-usa.com/product/jobst-farrowwrap-classic-armpiece/; Jul. 18, 2018.

Juzo Arm Compression Wrap; http://www.juzousa.com/Products/Product-Detail?ID= 70; date unknown, at least prior to applicant's filing date of Feb. 1, 2018.

MedAssist ArmAssist by SIGVARIS; http://www.lymphedemaproducts.com/products/medassist-armassist.html; at least as of Oct. 17, 2017.

MedaFit Arm by SIGVARIS; https://www.sigvaris.com/usa/en-us/product/medafit; at least as of Jun. 10, 2017.

CompreSleeve Arm by SIGVARIS; https://www.sigvaris.com/usa/en-us/product/compresleeve; at least as of Jun. 10, 2017.

Notice of Allowance received for U.S. Appl. No. 29/635,709 dated Sep. 5, 2019, 18 pages.

International Search Report for International Application No. PCT/EP2018/051917 dated Mar. 12, 2018.

Non-Final Office Action received for U.S. Appl. No. 15/443,308 dated May 31, 2019, 28 pages.

Non-Final Office Action received for U.S. Appl. No. 15/443,308 dated Nov. 18, 2019, 17 pages.

Non-Final Office Action received for U.S. Appl. No. 15/808,092 dated Jan. 10, 2020, 32 pages.

International Search Report and Written Opinion received for PCT Application Serial No. PCT/US2019/045792 dated Oct. 28, 2019, 8 pages.

International Preliminary Report on Patentability received for PCT Application Serial No. PCT/EP2018/051917 dated Jun. 5, 2019, 10 pages.

International Search Report and Written Opinion received for PCT Application Serial No. PCT/EP2018/079569 dated Feb. 4, 2019, 8 pages.

International Search Report and Written Opinion issued in corresponding International Application No. PCT/EP2017/072213 dated Nov. 10, 2017.

International Preliminary Report on Patentability received for PCT Application Serial No. PCT/EP2017/072213 dated Apr. 4, 2019, 8 pages.

International Search Report and Written Opinion issued in corresponding International Application PCT/EP2017/072211 dated Feb. 1, 2018.

(56) References Cited

OTHER PUBLICATIONS

International Preliminary Report on Patentability received for PCT Application Serial No. PCT/EP2017/072211 dated Apr. 4, 2019, 16 pages.

* cited by examiner

Table 1

| CEAP classification of chronic venous disease | Clinical classification |
|---|---|
| C0 | No visible or palpable signs of venous disease |
| C1 | Telangiectasies or reticular veins |
| C2 | Varicose veins |
| C3 | Edema |
| C4a | Pigmentation or eczema |
| C4b | Lipodermatosclerosis or athrophie blanche |
| C5 | Healed venous ulcer |
| C6 | Active venous ulcer |

METHODS AND SYSTEMS FOR FABRICATING, EVALUATING AND IMPROVING THERAPEUTIC COMPRESSION GARMENTS

TECHNICAL FIELD

The invention generally relates to systems and methods for designing, fabricating, selecting, evaluating and/or improving therapeutic compression garments for patients or other individuals (e.g., athletes) using compression garments.

BACKGROUND

Several publications may be referenced in this application. The cited references describe the state of the art to which this invention pertains and are hereby incorporated by reference, particularly the systems and methods set forth in the detailed description and figures of each reference.

Compression garments can be used to prevent and/or treat Chronic Venous Disorders (CVD), edema and a number of conditions that cause swelling in patient body parts or body areas.

CVD occurs when the veins are not working effective and it becomes increasingly difficult for the blood to pass through the vein walls or valves to flow back to the heart. Compression garment provides external compression and improves venous return.

Edema may arise from a variety of illnesses and conditions, including venous valvular insufficiency, postphlebotic syndrome, and lymphedema. Edema presents as excessive interstitial fluid accumulation, may arise from a variety of illnesses and conditions, including venous valvular insufficiency, post-phlebitic syndrome, posttraumatic, swelling, postoperative swelling, congestive heart failure-related hypoalbuminemia-related swelling, drug induced swelling, and lymphedema. Compression methods and products (e.g., garments) control edema by reducing interstitial fluid. Specifically, for the treatment of edema-like conditions, compression garments can address patient body part or body area swelling by increasing transport and reducing stagnation of interstitial fluids. Such interstitial fluids operate to increase nutrient delivery to tissue, remove waste from tissues, reduce pain from swelling, and decrease the risk of infection.

Due to considerable variation in limb shapes and sizes, custom garments may typically be required for patients with Medically Complex Extremities (MCE). To facilitate the manufacture of these garments, various partially fabricated kits are often available for a therapist or fitter to customize and fit a patient. Typical compression garment kits require measuring the patient to indicate cutting locations on the compression garment, in a manner that takes time and provides limited accuracy. The position of the measurement on the patient may not exactly align with the location marked on the garment, and typically only two or three measurements are transferred to the garment.

For therapeutic use, that is, compression that is prescribed by a clinician for treatment of one or more medical indications, proper fitting of compression garments is important if only because ill-fitting garments will not provide the intended/prescribed amount of compression therapy to the person being treated.

Another concern in the design of a therapeutic compression garment is patient comfort. A compression garment may provide proper compression characteristics, but if the wearer experiences discomfort due to pinching, chaffing, budding, or other reasons, the patient is unlikely to be compliant in wearing the compression garment and, thus, may not achieve therapeutic benefits.

Existing methods of fabricating, fitting and evaluating compression garments for a specific patient and/or therapeutic need are problematic as a result of the variations of patient size, shape and morphology, therapeutic responses, therapeutic compliance, therapeutic indications and other factors.

SUMMARY OF INVENTION

The invention generally relates to methods and systems, subsystems, apparatuses, and devices adapted for designing, fabricating, selecting, evaluating and improving therapeutic compression garments for patients or individuals using compression garments.

One aspect of the invention relates to a method for making a therapeutic series of two or more therapeutic compression garments for a patient comprising:

a) acquiring digital images of a body part or body area of interest in a patient in need of compression therapy, the digital images including surface morphology of the selected body part or body area;

b) processing the digital images by a computing device to generate a first three-dimensional digital image of the selected body part or body area including the surface morphology;

c) providing a first compression garment selected, designed and/or fabricated using the first three-dimensional digital image, wherein the dimensions and/or properties of the first compression garment are based on, designed and/or fabricated using the first three-dimensional digital image and is configured to be therapeutically appropriate to provide the compression therapy to the patient;

d) acquiring digital images of the selected body part or body area after the patient has worn the first compression garment for a first period of time and processing the digital images by the computing device to generate a second three-dimensional digital image of the selected body part or body area and any surface morphology changes; and e) providing a second compression garment selected, designed and/or fabricated using the second three-dimensional digital image, wherein the second compression garment incorporates at least one compression level based on second three-dimensional digital image and is configured to be therapeutically appropriate to provide the improved compression therapy to the patient.

Another aspect of the invention relates to a method for providing a best fitting therapeutic compression garment for a patient comprising:

a) acquiring digital images of a body part or body area of interest in the patient in need of compression therapy, the selected body part or body area having a surface morphology;

b) processing the digital images by a computing device to generate a three-dimensional digital image of the selected body part or body area and generating a therapeutic diagnosis, wherein the therapeutic diagnosis is CVD, MCE or other patient health indication; and c) providing a compression garment based on the three-dimensional digital image and the therapeutic diagnosis, wherein the dimensions and/or properties of the compression garment is based on, designed and/or fabricated using the three-dimensional digital image and the therapeutic diagnosis and the at least one compression level is identified as therapeutically appropriate to provide the compression therapy to the patient.

Yet another aspect of the invention relates to method of monitoring compression garment therapy for a patient comprising:

a) acquiring digital images of a selected body part or body area of the patient receiving or in need of compression garment therapy, the selected body part or body area having a surface morphology;

b) processing the digital images by a computing device to generate a first three-dimensional digital image of the selected body part or body area;

c) acquiring digital images of the selected body part or body area of the patient after a first period of time and processing the digital images by the computing device to generate a second three-dimensional digital image of the selected body part or body area; and d) comparing the first three-dimensional digital image with the second three-dimensional digital image to generate a therapeutic assessment.

A still further aspect of the invention relates to systems, subsystems, apparatuses, and/or devices adapted and/or configured to perform one or more of the computer-based methods described herein.

The foregoing has outlined some of the aspects of the present invention. These aspects should be construed strictly as illustrative of some of the more prominent features and applications of the invention, rather than as limitations on the invention. Many other beneficial results can be obtained by modifying the embodiments within the scope of the invention. Accordingly, for other objects and a full understanding of the invention, refer to the summary of the invention, the detailed description describing the preferred embodiment in addition to the scope of the invention defined by the claims and the accompanying drawings. The unique features characteristic of this invention and operation will be understood more easily with the description and drawings. It is to be understood that the drawings are for illustration and description only and do not define the limits of the invention.

BRIEF DESCRIPTION OF THE DRAWINGS

The above-mentioned and other features of the inventions disclosed herein are described below with reference to the drawings of the preferred embodiments. The illustrated embodiments are intended to illustrate, but not to limit the inventions. The drawings contain the following figures.

DETAILED DESCRIPTION OF PREFERRED EMBODIMENTS

In the following description, for purposes of explanation, specific details are set forth in order to provide a thorough understanding of different aspects of the present invention. It will be evident, however, to one skilled in the art that the present invention as defined by the claims may include some or all of the features or embodiments herein described and may further include obvious modifications and equivalents of the features and concepts described herein.

Definitions:

"Compression Garment" as used herein refers to garments designed and adapted to provide therapeutic compression when worn by the individual. These garments can be elastic garments (e.g. circular-knit, flat-knit), inelastic garments (e.g. wraps) or pneumatic (e.g. inflatable) or other compression technology (e.g., materials adapted to change size/shape with electrical signals).

Figure 2:
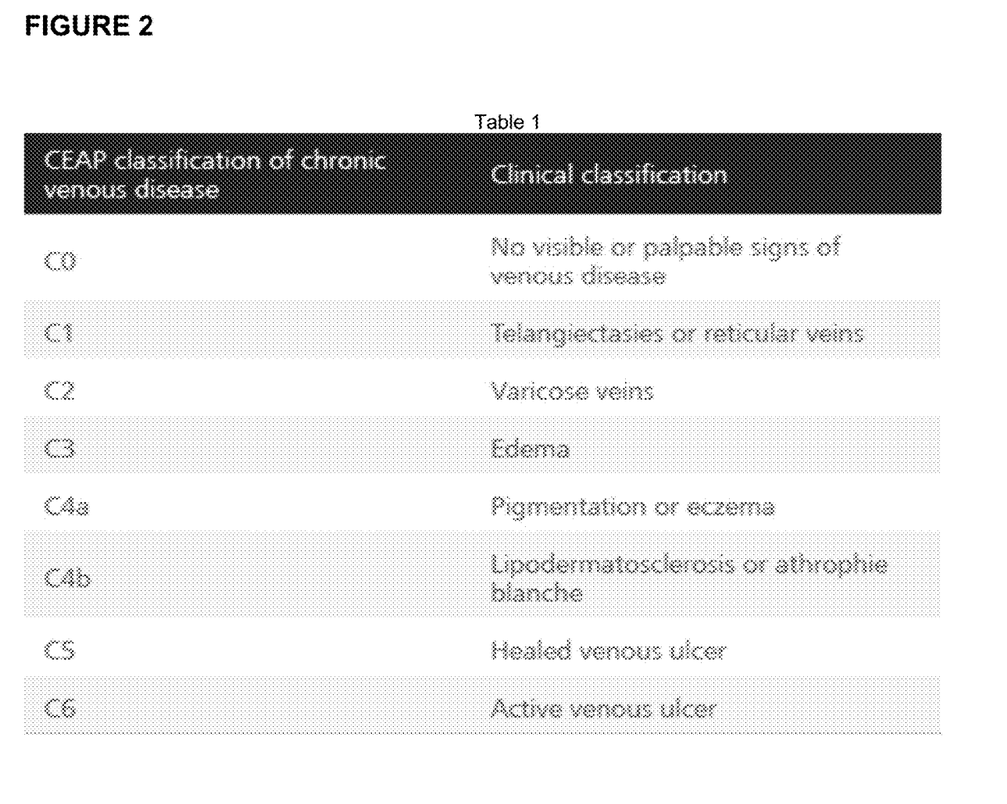
FIG. 2 shows Table 1 listing chronic venous disorders.

"CVD" means chronic venous disorders. The Comprehensive Classification System (CEAP) created by the committee of American Venous Forum in 1994 is the standard for classifying chronic venous disorders. Chronic venous disorders are listed in Table 1 as shown in FIG. 2 under Clinical Classification.

"MCE" means medically complex extremities. Patients having medically complex extremities are patients with severe/progresses veno-lymphatic disorders (i.e. CEAP-classes above C3 as well stage two and three of lymphedema).

"Other patient indication" includes indications about consumer/patient health that would benefit from therapeutic compression treatments (e.g. heavy legs, Deep Vein Thrombose (DVT), Venous Thromboembolism (VTE), etc.).

The invention relates to systems, apparatuses, and devices adapted to designing, fabricating, selecting, evaluating and improving therapeutic compression garments for patients or individuals using compression garments.

Figure 1:
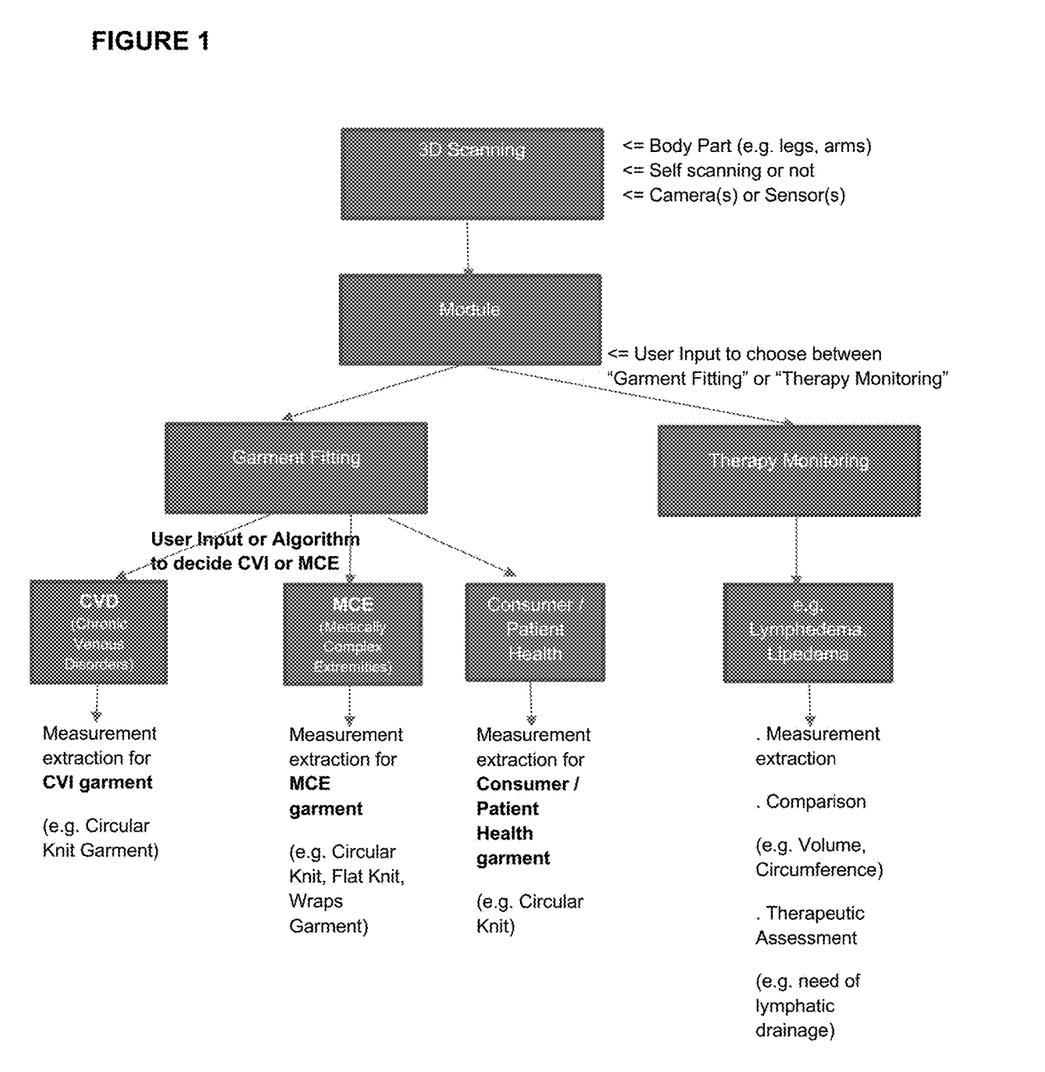
FIG. 1 is a flow diagram of methods for garment fitting and therapy monitoring and method for therapy monitoring according to one embodiment of the invention.

FIG. 1 is a flow diagram of a process sequence according to one embodiment of the invention showing a first step "3D Scanning" of the body part (e.g., leg or arm) either performed by self-scanning by the patient or user, by the caregiver (e.g., doctor or nurse) or operator (e.g., technician) or robotic system (e.g., robotic scanner) using one or more camera(s) and/or sensors (e.g., smartphone application, camera, scanner device or the like). FIG. 1 further shows Step 2 "Module" illustrating the preferred options of selecting either "garment fitting" or "therapy monitoring", preferably the option selected by a user input (e.g., the patient selects the option input on a computer device or smartphone).

As shown in FIG. 1, if "Garment Fitting" is selected, the additional options to select include (a) measurement extraction for chronic venous insufficiency or CVD (e.g., circular knit garment); (b) measurement extraction for medical complex extremities or MCE (e.g., circular knit, flat knit or wrap garment); or (c) measurement extraction for consumer and patient health garment (e.g., circular knit). According to one embodiment, a user (e.g., patient, caregiver or operator) selects options (a), (b) or (c). As shown in FIG. 1, if "Therapy Monitoring" is selected, the next step is measurement extraction for therapy monitoring (e.g., for lymphedema, lipedema, etc.) and preferably comprises comparing two or more sets of digital images, preferably acquired over time during the compression or other therapy (e.g., change in volume, circumference or the like of body part). Preferably, the next step also comprises a therapeutic assessment (e.g. need of lymphatic drainage, need for change in medication(s), etc.).

According to alternative embodiment, one or more computer-based algorithms make the selection based in the acquired digital images and/or other inputs or information.

For example, one embodiment comprises one or more of the following initial algorithms (e.g., first signing into the system or method).

Algorithm 1:

Step 1: Receive a security authorization request.

Step 2: Store the received security authorization request.

Algorithm 2:
Step 1: Digitally sign the received security authorization request using a private key
Step 2: Transmit the digitally signed security authorization request to an authentication server or application.

During the Scanning step and additional steps, one or more of the following algorithms may be used:
Algorithm 3:
Step 1: Receive instruction to initiate scanning.
Step 2: Store instruction to initiate scanning.
Algorithm 4:
Step 1: Receive digital images from scanning device.
Step 2: Store digital images.
Step 3: Stop scanning.
Algorithm 5:
Step 1: Receive image acquisition report.
Step 2: Store image acquisition report.
Algorithm 6:
Step 1: Receive module input for garment fitting or therapy monitoring.
Step 2: Store module input.
Algorithm 7:
Step 1: Processing digital images to general 3D image(s).
Step 2: Store 3D image(s).
Algorithm 8:
Step 1: Receive measurement extractions from 3D image(s).
Step 2: Store measurement extractions.
Algorithm 9:
Step 1: Receive diagnosis input for garment fitting
Step 2: Store diagnosis input.
Algorithm 10:
Step 1: Processing measurement extraction to provide a therapeutic compression garment.
Step 2: Store measurements.

According to the invention, the methods and system can be adapted or configured or customized, for example, the module can be adapted for (a) only Garment Fitting or (b) only Therapy Monitoring, or (c) only Garment Fitting for CVD, MCE and other patient indication.

One aspect of the invention relates to a method for making a therapeutic series of two or more therapeutic compression garments for a patient comprising:

a) acquiring digital images of a body part or body area of interest in a patient in need of compression therapy, the digital images including surface morphology of the selected body part or body area;

b) processing the digital images by a computing device to generate a first three-dimensional digital image of the selected body part or body area including the surface morphology;

c) providing a first compression garment selected, designed and/or fabricated using the first three-dimensional digital image, wherein the dimensions and/or properties of the first compression garment are based on, designed and/or fabricated using the first three-dimensional digital image and is configured to be therapeutically appropriate to provide the compression therapy to the patient;

d) acquiring digital images of the selected body part or body area after the patient has worn the first compression garment for a first period of time and processing the digital images by the computing device to generate a second three-dimensional digital image of the selected body part or body area and any surface morphology changes; and e) providing a second compression garment selected, designed and/or fabricated using the second three-dimensional digital image, wherein the second compression garment incorporates at least one compression level based on second three-dimensional digital image and is configured to be therapeutically appropriate to provide the improved compression therapy to the patient.

One embodiment of the invention further comprises:

f) acquiring digital images of the selected body part or body area of the patient after the patient has worn the second compression garment for a second period of time and processing the digital images by the computing device to generate a third three-dimensional digital image of the selected body part or body area and any additional surface morphology changes; and g) providing a third compression garment from the third three-dimensional digital image, wherein the dimensions and/or characteristics of the third compression garment are based on, designed and/or fabricated using the third three-dimensional digital image and is configured to be therapeutically appropriate to provide improved compression therapy to the patient.

Another embodiment further comprises:

h) acquiring digital images of the selected body part or body area of the patient after the patient has worn the third compression garment for a third period of time and processing the digital images by the computing device to generate a fourth three-dimensional digital image of the selected body part or body area and any additional surface morphology changes; and i) providing a fourth compression garment from the fourth three-dimensional digital image, wherein the dimensions and/or characteristics of the fourth compression garment are based on, designed and/or fabricated using the forth three-dimensional digital image and is configured to be therapeutically appropriate to provide improved compression therapy to the patient.

Preferably, the methods further comprise receiving a diagnosis input, by a computer or a user, selecting from the diagnosis options including (i) chronic venous disorders or CVD, (ii) medical complex extremities or MCE and/or (iii) other patient indication.

Preferably, the methods further comprise, prior to the processing the digital images by a computing device to generate the first three-dimensional digital image, selecting, by a computer or a user, therapy monitoring processing from the processing options (i) therapy monitoring or (ii) compression garment fitting. According to preferred embodiments, the diagnosis input is received by a user from a computer, smartphone or other computer device.

Preferably, the methods further comprise processing the digital images by the computing device to generate a first three-dimensional digital image including generating a patient diagnosis for the patient selecting from the options (i) CVD, (ii) MCE, and/or (iii) other patient indication.

Preferably, the methods further comprise processing the digital images by the computing device including generating circumference measurements, length measurements and topographic measurements of the selected body part or body area of the patient.

Preferably, the selected body part or body area is selected from the group consisting of: (i) lower body part or (ii) upper body part.

According to preferred embodiments, the selected body part or body area is selected from the group consisting of: (i) arm or portion of arm; (ii) leg or portion of leg; (iii) wrist, (iv) ankle, (v) chest, (vi) neck, (vii) knee, (viii) hand, or (ix) foot.

Preferably, the digital images of the selected body part or body area are acquired by the user (e.g., patient or an operator) or a robotic device moving an imaging device around the selected body part or body area of interest and wherein the operation of the imaging device can be controlled remotely. According to preferred embodiments, an image acquisition report is presented (preferably a 'real time' image) on a screen that is in operational engagement with the image capture device and wherein a digital image acquisition report is monitorable by the operator or by the device substantially in real time during the digital image acquisition step, wherein the image acquisition report includes information received about a three-dimensional reconstruction of the selected body part or body area, and wherein the operator or the device can adjust the digital image acquisition in response to the received information.

Preferably, the processing comprises generating shape description information for the selected body part or body area, wherein the generated shape description information comprises geometric information for the selected body part or body area, the geometric information being associated with the surface morphology of the selected body part or body area of the patient.

Preferably, the processing further comprises deriving measurement information for the selected body part or body area from the shape description information.

The "period of time" the compression garment is worn before the next digital image is acquired will depend on a number of factors including the patient's indication, the patient's schedule, the body part(s) being treated by the garment(s), the type of garment(s) and other factors.

According to one embodiment, the first period of time is greater than a day.

According to another embodiment, the first period of time is greater than one week.

According to another embodiment, the first period of time is greater than one month.

According to another embodiment, the second period of time is greater than a day.

According to another embodiment, the second period of time is greater than one week.

According to another embodiment, the second period of time is greater than one month.

Alternatively, the period of time or parameter tracked by the system or method is the number of hours or other accumulated time the patient has worn the compression garment.

The invention relates to compression garments and similar compression products and method of making and using the same. According to preferred embodiments, the therapeutic compression garment is selected from the group consisting of: flat knit compression garment, circular knit compression garment, and/or wraps compression garment (inelastic or short stretch wraps).

According to preferred embodiments of the methods described herein, the processing of the digital images by the computing device comprises generating shape description information for the selected body part or body area, wherein the generated shape description information comprises geometric information for the selected body part or body area. Preferably, the geometric information comprises surface morphology of the selected body part or body area of the patient. Preferably, the measurement information for the selected body part or body area can be derived from the shape description information.

According to preferred embodiments, the selected body part or body area is at least part of one arm or at least part of one leg.

According to preferred embodiments, the selected body part or body area is an upper body part or lower body part.

According to preferred embodiments of the methods described herein, the digital images are not acquired by rotation of an imaging device on a path about a fixed axis around the patient or by rotation of the patient on a platform.

According to preferred embodiments of the methods described herein, the digital images are acquired by either: (i) rotation of the device or operator around the body part or (ii) rotation of the patient.

According to preferred embodiments, the digital images are acquired by an operator moving an imaging device around the selected body part or body area of the patient. Preferably, the imaging device is free to move around the selected body part or body area with six degrees of freedom, unconstrained by a mounting or support assembly. Preferably, the operator observes a digital image acquisition report, preferably in substantially real time during the digital image acquisition step, wherein the digital image acquisition report includes information received about a three-dimensional (3D) reconstruction of the selected body part or body area, and wherein the operator can adjust the digital image acquisition in response to the received information about the 3D reconstruction. Preferably, the digital image acquisition report is presented to the operator on a screen that is in operational engagement with the imaging device.

According to preferred embodiments of the methods described herein, the compression garment comprises geometric features associated with the selected body part or body area that reduce pinching or chaffing of the patient and/or enable optimal garment fitting.

According to preferred embodiments of the methods described herein, the compression garment is in a form of an arm sleeve, circular knitted garment, flat knitted Garment, or wrap for the upper body. Preferably, the at least one compression level is incorporated in an area distal from a top end of the arm sleeve, and wherein the top end is proximal to either an elbow area or a shoulder area on the patient.

According to preferred embodiments of the methods described herein, the compression garment is in a form of a leg covering, circular knitted garment, flat knitted garment, or wrap (e.g. for lower body or torso).

According to preferred embodiments of the methods described herein, the at least one compression level is incorporated in an area distal to a top end of the leg covering, and wherein the top end is proximal to either a knee area or a thigh area on the patient.

Preferably, the at least part of the selected body part or body area substantially does not comprise a circular cross-sectional area.

Another aspect of the invention relates to a method for providing a best fitting therapeutic compression garment for a patient comprising:

a) acquiring digital images of a body part or body area of interest in the patient in need of compression therapy, the selected body part or body area having a surface morphology;

b) processing the digital images by a computing device to generate a three-dimensional digital image of the selected body part or body area and, preferably, generating a therapeutic diagnosis, wherein the therapeutic diagnosis is CVD, MCE or other patient health indication; and c) providing a compression garment based on the three-dimensional digital image and the therapeutic diagnosis, wherein the dimensions and/or properties of the compression garment is based on, designed and/or fabricated using the three-dimensional digital image and the therapeutic diagnosis and the at least one compression level is identified as therapeutically appropriate to provide the compression therapy to the patient.

Another aspect of the invention relates to a method of monitoring compression garment therapy for a patient comprising:

a) acquiring digital images of a selected body part or body area of the patient receiving or in need of compression garment therapy, the selected body part or body area having a surface morphology;

b) processing the digital images by a computing device to generate a first three-dimensional digital image of the selected body part or body area;

c) acquiring digital images of the selected body part or body area of the patient after a first period of time and processing the digital images by the computing device to generate a second three-dimensional digital image of the selected body part or body area; and d) comparing the first three-dimensional digital image with the second three-dimensional digital image to generate a therapeutic assessment.

Preferably, the method further comprises providing a replacement compression garment based on the second three-dimensional digital image and the therapeutic assessment, wherein the dimensions and/or properties of the fabricated replacement compression garment is based on, designed and/or fabricated using the second three-dimensional digital image and therapeutic assessment and is configured as therapeutically appropriate to provide compression therapy to the patient.

Preferably, the therapeutic assessment includes one or more values selected from the group consisting of: change of volume, change of circumferences, oedema reduction measurement and/or assessment on the need of a new compression garment when the second three-dimensional digital image differs significantly from the first three-dimensional digital image.

Preferably, the therapeutic assessment includes one or more indications on complete decongestive therapy including an indication relating to the need of lymphatic drainage.

Another aspect of the invention relates to a method of making a therapeutic compression garment for a patient comprising:

a) acquiring digital images of a body part or body area of interest in the patient in need of compression therapy, the selected body part or body area having a surface morphology;

b) processing the digital images by a computing device to generate a three-dimensional digital image of the selected body part or body area and, preferably, generating a therapeutic diagnosis, wherein the therapeutic diagnosis is CVD, MCE or other patient health indication;

c) generating a design for the therapeutic compression garment using the three-dimensional digital image; and d) fabricating the therapeutic compression garment based on the design.

Another aspect of invention relates to a system, subsystem, apparatus, and/or device adapted and/or configured for designing, fabricating, selecting, evaluating and improving therapeutic compression garments for patients or individuals using compression garments.

One embodiment relates to an apparatus adapted to perform one or more of the methods described herein, the apparatus comprising: (a) a sensor module (e.g., camera) adapted to acquire the digital images of the body part or body area of interest, the digital images including surface morphology of the selected body part or body area; and (b) a data processor adapted to receive signals output from the sensor module and to generate the three-dimensional digital image of the selected body part or body area including the surface morphology, wherein the signals represent detected digital images.

Preferably, the apparatus further comprises a computer device, for controlling operation of the apparatus. According to preferred embodiments, the apparatus further comprises an operator control device coupled to the computer device. According to preferred embodiments, the apparatus further comprises a viewing screen coupled to the computer device for displaying the digital images and/or the three-dimensional digital image.

Preferably, the apparatus further comprises a network terminal for transmitting information to other locations.

Preferably, the apparatus further comprises a transmitter for transmitting information to other locations.

Preferably, the apparatus further comprises a memory for storing one or more programs for execution by the data processor and/or storing the digital images and/or the three-dimensional digital image.

Preferably, the apparatus further comprises a connector adapted to connect to a cloud for storing the one or more programs for execution by the data processor and/or storing the digital images and/or the three-dimensional digital image.

All or part of the systems, methods and techniques described herein may be implemented as a computer program product that includes instructions that are stored on one or more non-transitory machine-readable storage media, and that are executable on one or more processing devices. All or part of the systems and techniques described herein may be implemented as an apparatus, method, or electronic system that may include one or more processing devices and memory to store executable instructions to implement the stated functions.

Various implementations of the systems, methods and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user (e.g., patient, doctor, nurse, therapist, or operator), the systems and techniques described here can be implemented on a computer having a display device (e.g., a CRT (cathode ray tube) or LCD (liquid crystal display) monitor) for displaying information to the user and a keyboard and/or a pointing device (e.g., a mouse or a trackball) and/or touchable screen (e.g., smartphone or computer tablet) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of implementations have been described. Nevertheless, it will be understood that various modifications may be made without departing from the spirit and scope of the invention.

In addition, the logic flows depicted in the figure(s), or in the algorithms described above, do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

Elements of different implementations described herein may be combined to form other implementations not specifically set forth above. Elements may be left out of the processes, computer programs, Web pages, etc. described herein without adversely affecting their operation. Furthermore, various separate elements may be combined into one or more individual elements to perform the functions described herein.

Thus, the systems and methods may be provided on many different types of computer-readable media including computer storage mechanisms (e.g., CD-ROM, diskette, RAM, flash memory, computer's hard drive, cloud, etc.) that contain instructions for use in execution by a processor to perform the methods' operations and/or algorithms and implement the systems described herein.

Exemplary embodiments of the present invention can be implemented using one or more program modules and data storage units. As used herein, the term "modules", "program modules", "components", "systems", "tools", "utilities", and the like include routines, programs, objects, components, data structures, and instructions, or instructions sets, and so forth that perform particular tasks or implement particular abstract data types. As can be appreciated, the modules refer to computer-related entities that can be implemented as software, hardware, firmware and/or other suitable components that provide the described functionality, and which may be loaded into memory of a machine embodying an exemplary embodiment of the present invention. Aspects of the modules may be written in a variety of programming languages, such as C, C++, Java, etc. As used herein, the terms "data storage unit," "data store", "storage unit", and the like can refer to any suitable memory device that may be used for storing data, including manual files, machine readable files, and databases (including cloud-based storage). The functionality provided by exemplary embodiments can be combined and/or further partitioned. The modules and/or storage units can all be implemented and run on the same computing system or they can be implemented and run on different computing systems. For example, one or modules can be implemented on a personal computer operated by a user while other modules can be implemented on a remote server and accessed via a network.

With respect to the appended claims, unless stated otherwise, the term "first" does not, by itself, require that there also be a "second". Moreover, reference to only "a first" and "a second" does not exclude additional items or steps.

While the particular computer-based systems and methods described herein and described in detail are fully capable of attaining the above-described objects and advantages of the invention, it is to be understood that these are the presently preferred embodiments of the invention and are thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular means "one or more" and not "one and only one", unless otherwise so recited in the claim.

Moreover, the various features of the representative examples and the dependent claims may be combined in ways that are not specifically and explicitly enumerated in order to provide additional useful embodiments of the present teachings. It is also expressly noted that all value ranges or indications of groups of entities disclose every possible intermediate value or intermediate entity for the purpose of original disclosure, as well as for the purpose of restricting the claimed subject matter.

As used herein, the singular forms "a", "an", and "the" are intended to include the plural forms as well, unless the content clearly indicates otherwise. It will be further understood that the terms "comprises", "includes", and "comprising", when used in this specification, specify the presence of stated features, integers, steps, operations, elements, components, and/or groups thereof.

The scope of the present devices, systems and methods, etc., includes both means plus function and step plus function concepts. However, the claims are not to be interpreted as indicating a "means plus function" relationship unless the word "means" is specifically recited in a claim, and are to be interpreted as indicating a "means plus function" relationship where the word "means" is specifically recited in a claim. Similarly, the claims are not to be interpreted as indicating a "step plus function" relationship unless the word "step" is specifically recited in a claim, and are to be interpreted as indicating a "step plus function" relationship where the word "step" is specifically recited in a claim.

It is understood that the embodiments described herein are for the purpose of elucidation and should not be considered limiting the subject matter of the disclosure. Various modifications, uses, substitutions, combinations, improvements, methods of productions without departing from the scope or spirit of the present invention would be evident to a person skilled in the art.

The invention claimed is:

1. A method for making a therapeutic series of two or more therapeutic compression garments for a patient comprising:
   a) acquiring digital images of a body part or body area of interest in a patient in need of compression therapy, the digital images including surface morphology of the selected body part or body area;
   b) processing the digital images by a computing device to generate a first three-dimensional digital image of the selected body part or body area including the surface morphology;
   c) providing a first compression garment selected, designed and/or fabricated using the first three-dimensional digital image, wherein the dimensions and/or properties of the first compression garment are based on, designed and/or fabricated using the first three-dimensional digital image and is configured to be therapeutically appropriate to provide the compression therapy to the patient;
   d) acquiring digital images of the selected body part or body area after the patient has worn the first compression garment for a first period of time and processing the digital images by the computing device to generate a second three-dimensional digital image of the selected body part or body area and any surface morphology changes; and
   e) providing a second compression garment selected, designed and/or fabricated using the second three-dimensional digital image, wherein the second compression garment incorporates at least one compression level based on second three-dimensional digital image and is configured to be therapeutically appropriate to provide the improved compression therapy to the patient.

2. The method of claim 1, further comprising:
   f) acquiring digital images of the selected body part or body area of the patient after the patient has worn the second compression garment for a second period of time and processing the digital images by the computing device to generate a third three-dimensional digital image of the selected body part or body area and any additional surface morphology changes; and
   g) providing a third compression garment from the third three-dimensional digital image,
   wherein the dimensions and/or characteristics of the third compression garment are based on, designed and/or fabricated using the third three-dimensional digital image and is configured to be therapeutically appropriate to provide improved compression therapy to the patient.

3. The method of claim 1, further comprising receiving a diagnosis input, by a computer or a user, selecting from the diagnosis options including (i) CVD, (ii) MCE, and/or (iii) other patient indication.

4. The method of claim 1, further comprising, prior to the processing of the digital images by a computing device to generate the first three-dimensional digital image, selecting, by a computer or a user, from the processing options (i) therapy monitoring or (ii) compression garment fitting.

5. The method of claim 3, wherein the diagnosis input is received by a user from a computer, smartphone or other computer device.

6. The method of claim 1, wherein the processing of the digital images by the computing device to generate a first three-dimensional digital image including a patient diagnosis for the patient, includes selecting from the options (i) CVD, (ii) MCE, and/or (iii) other patient indication.

7. The method of claim 1, wherein the processing the digital images by the computing device includes generating circumference measurements, length measurements and topographic measurements of the selected body part or body area of the patient.

8. The method of claim 1, wherein the selected body part or body area is selected from the group consisting of: (i) lower body part or (ii) upper body part and the first period of time is greater than one week.

9. The method of claim 1, wherein the selected body part or body area is selected from the group consisting of: (i) arm or portion of arm; (ii) leg or portion of leg; (iii) wrist, (iv) ankle, (v) chest, (vi) neck, (vii) knee, (viii) hand, or (ix) foot.

10. The method of claim 1, wherein the digital images of the selected body part or body area are acquired by a user or a robotic device moving an imaging device around the selected body part or body area of interest and wherein the operation of the imaging device can be controlled remotely.

11. The method of claim 10, wherein an image acquisition report is presented on a screen that is in operational engagement with the image capture device and wherein a digital image acquisition report is monitorable by the operator or by the device substantially in real time during the digital image acquisition step, wherein the image acquisition report includes information received about a three-dimensional reconstruction of the selected body part or body area, and wherein the operator or the device can adjust the digital image acquisition in response to the received information.

12. The method of claim 1, wherein the processing comprises generating shape description information for the selected body part or body area, wherein the generated shape description information comprises geometric information for the selected body part or body area, the geometric information being associated with the surface morphology of the selected body part or body area of the patient.

13. The method of claim 1, wherein said processing further comprises deriving measurement information for the selected body part or body area from the shape description information.

14. The method of claim 1, wherein the processing of the digital images by the computing device comprises generating shape description information for the selected body part or body area, wherein the generated shape description information comprises geometric information for the selected body part or body area and wherein said processing generates two or more sets of three-dimensional digital images of the selected body part or body area and generates a therapeutic diagnosis comparing the two or more sets of three-dimensional digital images.

15. An apparatus adapted to perform the methods of claim 1, the apparatus comprising:
   a sensor module adapted to acquire the digital images of the body part or body area of interest, the digital images including surface morphology of the selected body part or body area; and
   a data processor adapted to receive signals output from the sensor module and to generate the three-dimensional digital image of the selected body part or body area including the surface morphology, wherein the signals represent detected digital images.

16. A method for providing a best fitting therapeutic compression garment for a patient comprising:
  a) acquiring digital images of a body part or body area of interest in the patient in need of compression therapy, the selected body part or body area having a surface morphology;
  b) processing the digital images by a computing device to generate a three-dimensional digital image of the selected body part or body area and generating a therapeutic diagnosis, wherein the therapeutic diagnosis is CVD, MCE or other patient health indication;
  c) providing a first compression garment based on the three-dimensional digital image and the therapeutic diagnosis, wherein the dimensions and/or properties of the first compression garment is based on, designed and/or fabricated using the three-dimensional digital image and the therapeutic diagnosis and the at least one compression level is identified as therapeutically appropriate to provide the compression therapy to the patient; and
  d) acquiring digital images of the selected body part or body area after the patient has worn the first compression garment for a first period of time and processing the digital images by the computing device to generate a second three-dimensional digital image of the selected body part or body area and any surface morphology changes; and
  e) providing a second compression garment selected, designed and/or fabricated using the second three-dimensional digital image, wherein the second compression garment incorporates at least one compression level based on second three-dimensional digital image and is configured to be therapeutically appropriate to provide the improved compression therapy to the patient.

17. A method of monitoring compression garment therapy for a patient comprising:
  a) acquiring digital images of a selected body part or body area of the patient receiving or in need of compression garment therapy, the selected body part or body area having a surface morphology and selected from the group consisting of: (i) arm or portion of arm; (ii) leg or portion of leg; (iii) wrist, (iv) ankle, (v) chest, (vi) neck, (vii) knee, (viii) hand, or (ix) foot;
  b) processing the digital images by a computing device to generate a first three-dimensional digital image of the selected body part or body area;
  c) acquiring digital images of the selected body part or body area of the patient after a first period of time and processing the digital images by the computing device to generate a second three-dimensional digital image of the selected body part or body area;
  d) comparing said first three-dimensional digital image with said second three-dimensional digital image to generate a therapeutic assessment; and
  e) providing a replacement compression garment based on the second three-dimensional digital image and the therapeutic assessment, wherein the dimensions and/or properties of the fabricated replacement compression garment is based on, designed and/or fabricated using the second three-dimensional digital image and therapeutic assessment and is configured as therapeutically appropriate to provide compression therapy to the patient.

18. The method of claim 17, wherein therapeutic assessment includes one or more values selected from the group consisting of: change of volume, change of circumferences, oedema reduction measurement and/or assessment on the need of a new compression garment when the second three-dimensional digital image differs significantly from the first three-dimensional digital image.

19. The method of claim 17, wherein therapeutic assessment includes one or more indications on complete decongestive therapy including an indication relating to the need of lymphatic drainage.

* * * * *